(12) United States Patent
Greenlee

(10) Patent No.: US 11,730,920 B2
(45) Date of Patent: Aug. 22, 2023

(54) SAFETY CATHETER USING A SECONDARY BALLOON AND TERTIARY LUMEN

(71) Applicant: Biological Innovations LLC, Sterling Heights, MI (US)

(72) Inventor: Jason Richard Greenlee, Beverly Hills, MI (US)

(73) Assignee: Jason Richard Greenlee, Davidson, NC (US)

( * ) Notice: Subject to any disclaimer, the term of this patent is extended or adjusted under 35 U.S.C. 154(b) by 302 days.

(21) Appl. No.: 16/952,834

(22) Filed: Nov. 19, 2020

(65) Prior Publication Data

US 2021/0146093 A1    May 20, 2021

Related U.S. Application Data

(60) Provisional application No. 62/938,160, filed on Nov. 20, 2019.

(51) Int. Cl.
*A61M 25/10* (2013.01)
*A61M 25/00* (2006.01)
*A61M 1/00* (2006.01)

(52) U.S. Cl.
CPC ............ *A61M 25/003* (2013.01); *A61M 1/84* (2021.05); *A61M 25/1011* (2013.01); *A61M 25/10186* (2013.11); *A61M 2210/1085* (2013.01)

(58) Field of Classification Search
CPC ...... A61M 1/84; A61M 25/00; A61M 25/003; A61M 25/04; A61M 25/008;
(Continued)

(56) References Cited

U.S. PATENT DOCUMENTS 3,378,011 A * 4/1968 Vitello ............ A61M 25/10184
                                                      604/920
3,543,758 A * 12/1970 McWhorter .... A61M 25/10187
                                                      604/920
(Continued)

FOREIGN PATENT DOCUMENTS

CN         113209454 A * 8/2021

OTHER PUBLICATIONS

"Foley Catheter", online: https://en.wikipedia.org/wiki/Foley_catheter, Jun. 25, 2020, 5 pages, Wikimedia Foundation, Inc.

*Primary Examiner* — Benjamin J Klein
*Assistant Examiner* — Jihad Dakkak
(74) *Attorney, Agent, or Firm* — Behmke Innovation Group LLC; Kenneth J. Heywood; James E. Denker

(57) ABSTRACT

A catheter comprising an elongated member having a distal end and a proximal end. The proximal end defines a drainage inlet extending from an external wall of the elongated member into the elongated member. The elongated member defines a first lumen that connects the drainage inlet with a drainage outlet defined by the distal end. The catheter also includes an inflatable retention balloon defined by the external wall of the elongated member and located between the drainage inlet and the drainage outlet. The catheter further includes a fluid inlet valve that protrudes from the elongated member and defines a second lumen that extends from the fluid inlet valve through the elongated member and to the inflatable retention balloon. The catheter additionally includes a secondary balloon that protrudes from the elongated member, the elongated member defining a third lumen that extends from the inflatable retention balloon to the secondary balloon.

20 Claims, 5 Drawing Sheets

(58) Field of Classification Search
CPC .............. A61M 25/0017; A61M 25/10; A61M 25/1011; A61M 25/10183; A61M 25/10184; A61M 25/10186; A61M 27/008; A61M 2210/1085
See application file for complete search history.

(56) References Cited

U.S. PATENT DOCUMENTS

| | | |
|---|---|---|
| 3,543,759 A | 12/1970 | McWhorter |
| 4,264,312 A | 4/1981 | Cianci |
| 4,820,270 A | 4/1989 | Hardcastle et al. |
| 6,530,898 B1 * | 3/2003 | Nimkar ............... A61M 16/044 604/100.01 |
| 9,084,868 B2 | 7/2015 | Aaronson et al. |
| 9,937,318 B2 * | 4/2018 | Bonneau ........... A61M 25/0017 |

* cited by examiner

SAFETY CATHETER USING A SECONDARY BALLOON AND TERTIARY LUMEN

RELATED APPLICATION

This application claims priority to U.S. Provisional Appl. Ser. No. 62/938,160, filed Nov. 20, 2019, entitled SAFETY CATHETER USING A SECONDARY BALLOON AND TERTIARY LUMEN, by Jason Richard Greenlee, the contents of which are incorporated herein by reference.

TECHNICAL FIELD

The present invention relates generally to catheters and, more particularly, to safety catheters using a secondary balloon and having a tertiary lumen.

BACKGROUND

In general, catheters are medical devices that are used for a variety of purposes. These purposes include administering fluids into a subject, taking in vivo measurements from a subject (e.g., pressure measurements), draining fluids from a subject, and the like. For instance, a urinary catheter may be inserted into the bladder of a subject as a treatment protocol for sepsis, hematuria, during lengthy surgical procedures, in bed-bound subjects, for strict urine output recording, instillation of chemotherapeutic agents, or bladder decompression in acute and chronic urinary retention. To prevent a urinary catheter from becoming dislodged, many urinary catheters are configured with an inflatable balloon (e.g., a Foley catheter) that is inflated within the bladder of the subject after insertion, thereby retaining the catheter within the bladder, and deflated when it is time for removal.

Removing a urinary catheter without first completely deflating its retention balloon, or inflating the retention balloon prior to proper placement within sufficiently hollow viscera, can lead to traumatic injury to the subject, such as urethral stricture disease, life-threatening hematuria, fistula formation, etc. Traumatic, unintended urinary catheter extractions and inflations, have also been shown to affect hospital length-of-stay, decrease hospital quality scores, decrease patient satisfaction scores, and increase the rate of catheter-associated urinary tract infections (CAUTIs). Thus, it is absolutely critical for the retention balloon of a urinary catheter to be completely deflated prior to removal, and properly positioned prior to inflation. Despite the potential damage that can result from urinary catheters, many of the urinary catheters in use today rely solely on the diligence of the healthcare provider for placement and maintenance, or the subject's mental status in the case of unintended self-removal, to ensure that the retention balloon is properly managed.

SUMMARY

In various embodiments, a catheter is introduced that comprises an elongated member having a distal end and a proximal end. The proximal end defines a drainage inlet extending from an external wall of the elongated member into the elongated member. The elongated member defines a first lumen that connects the drainage inlet with a drainage outlet defined by the distal end. The catheter also includes an inflatable retention balloon defined by the external wall of the elongated member and located between the drainage inlet and the drainage outlet. The catheter further includes a fluid inlet valve that protrudes from the elongated member and defines a second lumen that extends from the fluid inlet valve through the elongated member and to the inflatable retention balloon. The catheter additionally includes a secondary balloon that protrudes from the elongated member, the elongated member defining a third lumen that extends from the inflatable retention balloon to the secondary balloon.

In one embodiment, the secondary balloon of the catheter protrudes from the elongated member at the distal end of the elongated member. In another embodiment, the fluid inlet valve protrudes from the elongated member at the distal end of the elongated member. In a further embodiment, the inflatable retention balloon is configured to inflate in response to fluid being injected into the fluid inlet valve. In an additional embodiment, fluid is shunted from the inflatable retention balloon towards the distal end of the elongated member and into the secondary balloon via the third lumen. In another embodiment, fluid is shunted in response to an external force being applied to the inflatable retention balloon resulting from an attempt to remove the catheter from a subject while the inflatable retention balloon is inflated. In a further embodiment, the fluid is shunted in response to an external force being applied to the inflatable retention balloon resulting from the catheter being improperly inserted into a subject. In an additional embodiment, the secondary balloon remains ex vivo to a subject while the inflatable retention balloon retains the drainage inlet of the elongated member in a hollow viscera of the subject. In another embodiment, the drainage outlet remains ex vivo to a subject while the inflatable retention balloon retains the drainage inlet of the elongated member in a urinary bladder of the subject, and wherein urine in the urinary bladder flows into the drainage inlet and out of the drainage outlet via the first lumen. In yet another embodiment, the drainage outlet has a diameter larger than that of the first lumen. In an additional embodiment, the first lumen has a larger diameter than that of the second lumen and of the third lumen.

In various embodiments, a method comprises receiving, via a fluid inlet valve of a catheter a first fluid injected into a second lumen defined by the catheter, the catheter also defining a first lumen that connects a drainage inlet at a proximal end of the catheter to a drainage outlet at a distal end of the catheter. The method also comprises inflating a retention balloon of the catheter by conveying the first fluid from the second lumen into the retention balloon, the retention balloon being located between the drainage inlet and the drainage outlet. The method further comprises draining a second fluid from a subject by conveying the second fluid from the drainage inlet to the drainage outlet via the first lumen. The method additionally comprises shunting, via a third lumen of the catheter and in response to an external force applied to the retention balloon, the first fluid from the retention balloon into a secondary balloon of the catheter.

In various embodiments, a catheter comprises means for retaining the catheter in a hollow viscera of a subject. The catheter also comprises means for draining a first liquid from the hollow viscera of the subject. The catheter further comprises means for inflating, with an inflation means, the means for retaining the catheter in the hollow viscera of the subject. The catheter additionally comprises means for shunting the fluid from the means for retaining the catheter in the hollow viscera of the subject.

BRIEF DESCRIPTION OF THE DRAWINGS

The embodiments herein may be better understood by referring to the following description in conjunction with the accompanying drawings in which like reference numerals indicate identically or functionally similar elements, of which.

DETAILED DESCRIPTION

Figure 1A:
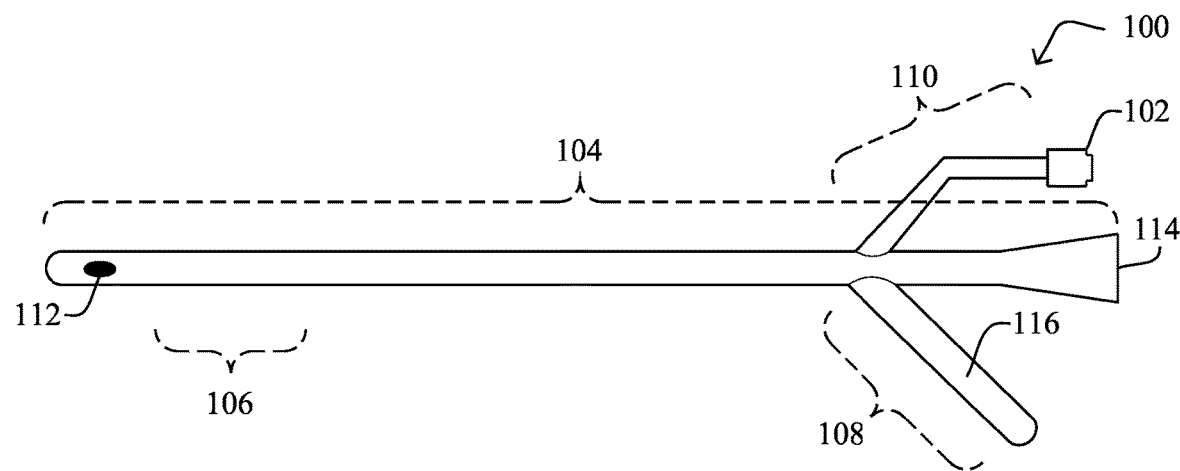
FIGS. 1A-1C illustrate exemplary views of a safety catheter, according to various embodiments.

In the following description, the term "subject" refers to a human or non-human animal, such as a primate, mammal, or other vertebrate. The term "patient" refers to a subject that is undergoing a medical procedure.

In the following description, the term "proximal" generally refers to a position on a catheter that is intended to be inserted into a subject and retained in vivo, during use. In contrast, the term "distal" generally refers to the end of the catheter opposing that of the proximal end and intended to remain ex vivo to the subject, during use.

As noted above, improper use of many catheters available today can lead to traumatic injury to the subject. Currently, traumatic urinary catheter balloon inflation injury prevention is directed at clinical evaluation, prior to catheterization, to determine whether the patient is a candidate for an indwelling urinary catheter. Commonly, unpredictable patient factors including dementia, delirium, late-day confusion, prostate enlargement, urethral narrowing, transfer during surgery, transport while in the hospital, or medical professional inexperience, result in the unintended traumatic extraction or balloon inflation of an indwelling urinary catheter. When this occurs, the fluid-filled retention balloon, which is meant to be within sufficiently hollow viscera, is misplaced into the urethra of the patient. Typically, an expanded retention balloon of a catheter has a diameter approximately between three and five centimeters, depending on the fluid volume, while the average urethra is approximately one centimeter in diameter. Thus, any attempt to remove a catheter with an inflated retention balloon, or inflate the retention balloon within the urethra, can result in significant pain, bleeding, scarring of native tissue, hospital admission, prolonged hospital course, and require the involvement of surgical specialists. Invariably, the trauma to the urethra can result in additional surgical procedures, and prolonged indwelling catheter time (7-14 days), as the urethra heals. The prolonged catheter time only perpetuates the cycle of potential injury and catheter-associated urinary tract infections (CAUTIs), making the treatment of these idiopathic sequelae very complicated. Consequences of untreated intraurethral urinary catheter balloon injury include urinary obstruction, blood loss anemia, infection, renal failure, and death.

Prior attempts to design a safety catheter, or a less traumatic catheter, typically focused on burstable balloons, membranes that rupture under pressure, or inlet arms. To date, however, clinical relevance of these approaches has not been achieved. Indeed, the fracturing of material within the subject can result in foreign-bodies remaining in vivo, serving as a nidus of infection, and calcification, in the urinary tract. This can result in an obstruction of the urinary tract, sepsis, renal failure, and possibly death.

The present invention mitigates the soft tissue damage caused by a displaced, or improperly placed, catheter. Advantageously, the catheter introduced herein is particularly ideal for subjects that are identified as high-risk for urethral injury, prior to placement. However, use of the catheter introduced herein is not limited as such and may be used across a wide range of subjects to prevent unintentional catheter extraction and inflation injuries in otherwise healthy patients. If a significant force is placed on the catheter, the retention balloon will deflate, or fail to inflate, allowing the balloon to comply with surrounding soft tissue. If completely or partially displaced out of the urethra, a new catheter can easily be replaced without the complications of a severely traumatized passageway. In the event the catheter retention balloon is not completely inserted in the bladder, or sufficiently hollow viscera, the catheter balloon will not inflate by shunting fluid ex vivo to the secondary balloon.

Figure 1B:
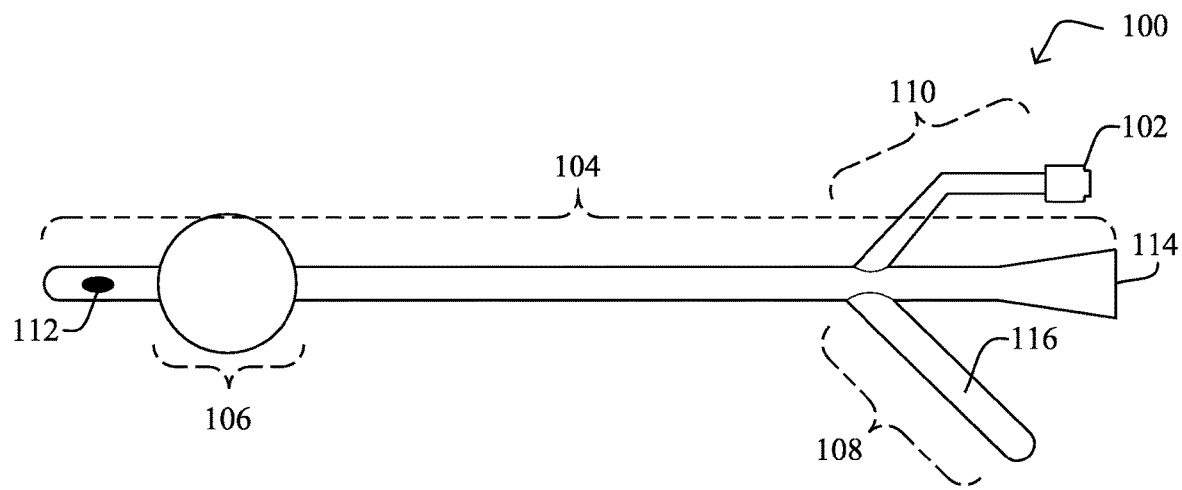
Figure 1C:
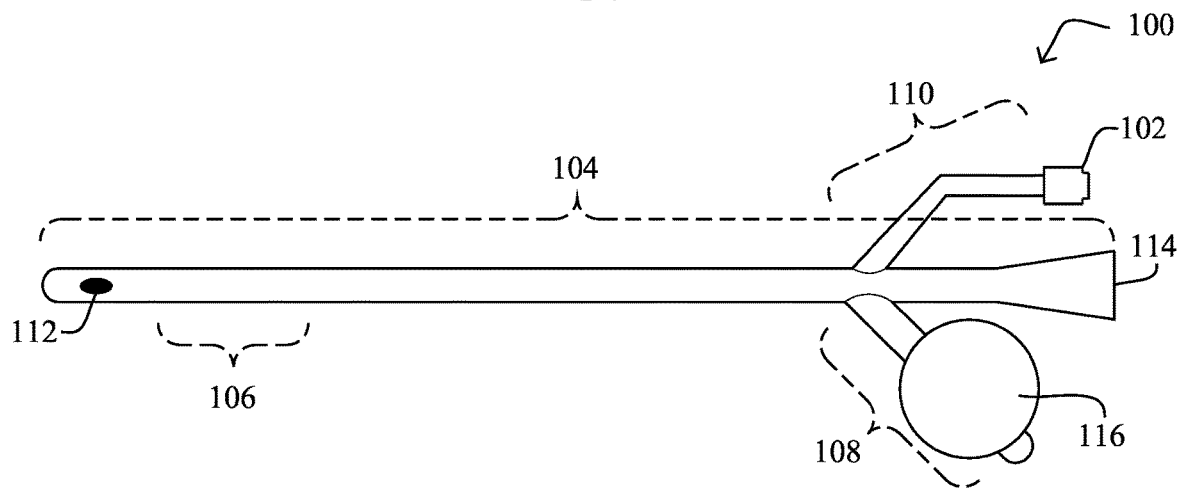

FIGS. 1A-1C illustrate exemplary views of a safety catheter 100, according to various embodiments. As shown in FIG. 1A, catheter 100 may generally take the form of a tubular membrane that includes a distal end and a proximal end. In various embodiments, catheter 100 may be constructed from vinyl (e.g., polyvinyl chloride, etc.), plastic, silicone, rubber, latex, nylon, polyurethane, polyethylene terephthalate, elastomers, combinations thereof, or any other suitable material.

At the core of catheter 100 is an elongated member 104 having a drainage inlet 112 at its proximal end that extend through the external wall of elongated member 104 and into a primary drainage lumen that extends internally towards the distal end of elongated member 104 and terminates at a drainage outlet 114. During use of catheter 100, this allows a fluid, such as urine, to enter drainage inlet 112, situated in vivo of the subject, and drain out of drainage outlet 114, located ex vivo of the subject. In other words, the proximal end of catheter 100 may be inserted into a hollow viscera of the subject, such as a urinary bladder, to allow a fluid within the subject to drain out of the subject via drainage outlet 114. To this end, in some embodiments, drainage outlet 114 may take the form of a flared end of elongated member 104 to allow for connection to a fluid collection reservoir. To facilitate this, drainage outlet 114 may have a larger diameter than that of the drainage lumen, in some embodiments.

In further embodiments, catheter 100 may instead be used to provide therapeutics or other fluids to the subject. For instance, a chemotherapeutic agent may be applied to the subject by using drainage outlet 114 as an inlet for the first lumen of elongated member 104 and drainage inlet 112 as the outlet for the agent.

In various embodiments, catheter 100 may also include an inflatable retention balloon 106 that serves to retain the proximal end of catheter 100 within the subject, when inflated. For instance, when the proximal end of catheter 100 is inserted into the bladder of a subject, inflation of retention balloon 106 will prevent catheter 100 from becoming dislodged and slipping out of the bladder.

FIG. 1B illustrates an example view of catheter 100 with retention balloon 106 inflated. By inflating retention balloon 106 in vivo, the diameter of retention balloon 106 will increase to a size that prevents the proximal end of catheter 100 from exiting the hollow viscera of the subject. As would be appreciated, retention balloon 106 may be located radially within elongated member 104 from the primary drainage lumen that connects drainage inlet 112 and drainage outlet 114. In other words, the primary drainage lumen of catheter 100 may traverse beneath, or through, retention balloon 106 to drainage outlet 114, without being in fluid communication with one another, as described in greater detail below.

In various embodiments, catheter 100 may include a fluid inlet valve 102 at its distal end that is connected to retention balloon 106 via a second lumen which extends from distal fluid inlet valve 102 and through elongated member 104 into retention balloon 106. In some embodiments, fluid inlet valve 102 may be connected to elongated member 104 via a hollow, first branch 110 that protrudes at the distal end of elongated member 104. After the proximal end of catheter 100 is inserted into the subject, fluid may be injected into fluid inlet valve 102 (e.g., via a syringe), thereby forcing fluid through the second lumen of catheter 100 and into retention balloon 106. In response, retention balloon 106 will inflate as its fluid volume increases, thereby retaining the proximal end of catheter 100 in the hollow viscera of the subject.

As would be appreciated, deflation of retention balloon 106 may be accomplished by reversing its inflation procedure. Namely, a syringe may be inserted into fluid inlet valve 102 and used to drain fluid from retention balloon 106. As the fluid volume in retention balloon 106 decreases, so too will its diameter. When retention balloon 106 has been deflated, as depicted in FIG. 1A, it can then be removed from the subject, safely.

According to various embodiments, catheter 100 may also include a secondary balloon 116 (i.e., a reservoir) at its distal end that is in connection with retention balloon 106 via a third lumen that is separate from the lumen that connects fluid inlet valve 102 to retention balloon 106 and from the lumen that connects drainage inlet 112 to drainage outlet 114. In some embodiments, as shown, secondary balloon 116 may be located along a branch 108 that protrudes from elongated member 104 at the distal end of catheter 100. Similar to retention balloon 106, secondary balloon 116 may be inflated in response to fluid entering its internal chamber via the tertiary lumen of catheter 100. In some embodiments, the deflated form of retention balloon 106 may have an external diameter similar to that of the rest of branch 108. In other embodiments, secondary balloon 116 may have an external diameter greater than that of the remainder of branch 108.

Construction of retention balloon 106 and/or secondary balloon 116 may be accomplished, for instance, by forming their respective outer walls with a thickness that is reduced from that of the outer walls of the secondary and tertiary lumens to which they are connected. Thus, fluid pressure from an injected fluid will cause the respective balloon to expand until the fluid is removed.

According to various embodiments, secondary balloon 116 may serve to prevent catheter 100 from inducing trauma to a subject, should retention balloon 106 remain inflated while in vivo. To this end, the tertiary lumen that connects retention balloon 106 to secondary balloon 116 may shunt fluid from retention balloon 106 into secondary balloon 116 when retention balloon 106 is subjected to an external force. Under such a condition, as shown in FIG. 1C, the fluid injected into retention balloon 106 via fluid inlet valve 102 may be shunted into secondary balloon 116, causing secondary balloon 116 to inflate and providing a visual indication to the person administering catheter 100.

For instance, if the person administering catheter 100 attempts to remove catheter 100 from the subject while retention balloon 106 is still inflated (e.g., as in FIG. 1B), the resulting force on retention balloon 106 will force the fluid within retention balloon 106 through the tertiary lumen of catheter 100 and into secondary balloon 116. This will give a visual indication to the person administering catheter 100 that retention balloon 106 needs to be deflated, first. In addition, as there is an additional pathway through which is the fluid is able to flow, this will mitigate the trauma caused to the subjected by the inflated retention balloon 106.

In another instance, secondary balloon 116 can also serve to provide a visual indication that catheter 100 was improperly inserted into the subject. For example, assume that the proximal end of catheter 100 is not fully within the bladder or other hollow viscera of the subject. In such a case, any attempt to inflate retention balloon 106 by injecting fluid into fluid inlet valve 102 will fail to inflate retention balloon 106 and cause damage to the subject. Instead, the force exerted by the tissue surrounding the deflated retention balloon 106 may exceed the resistance provided by the tertiary lumen and secondary balloon of catheter 100, thereby forcing the fluid through the tertiary lumen and into secondary balloon 116. Since secondary balloon 116 remain ex vivo to the subject, the resulting inflation of secondary balloon 116 will provide a visual indication to the person inserting catheter 100 that catheter 100 was not inserted properly.

Figure 2:
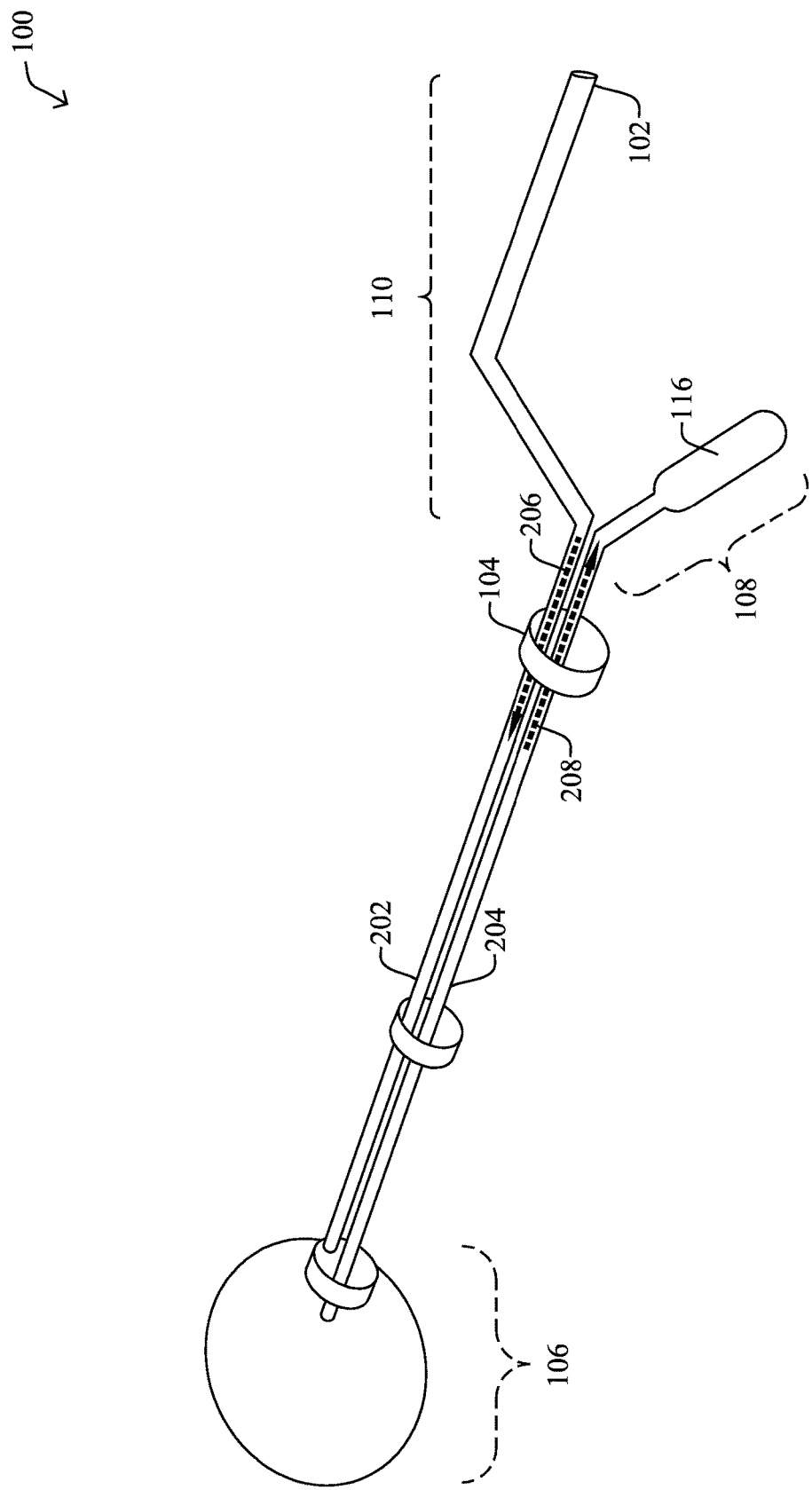
FIG. 2 illustrates a cutaway view of a safety catheter, according to various embodiments.

FIG. 2 illustrates a cutaway view of catheter 100 showing the inflation operations of retention balloon 106 and secondary balloon 116, according to various embodiments. As shown, a second lumen 202 may extend from fluid inlet valve 102 through branch 110 and internal to elongated member 104 to retention balloon 106. Similarly, a third lumen 204 extends from retention balloon 106 through elongated member 104 through branch 108 to secondary balloon 116.

When fluid is injected into fluid inlet valve 102, the fluid 206 will traverse second lumen 202 in the distal to proximal direction and into retention balloon 106, causing retention balloon 106 to inflate. For instance, the outer wall of retention balloon 106 may be of a lower thickness than that of second lumen 202 such that the fluid pressure that results from the injection of a fluid via fluid inlet valve 102 causes the outer wall of retention balloon 106 to expand.

In various embodiments, third lumen 204 may be configured to shunt fluid 208 from retention balloon 106 in the proximal to distal direction into secondary balloon 116, when sufficient external force is applied to retention balloon 106 (e.g., when an attempt is made to remove catheter 100 with retention balloon 106 still inflated, when an attempt is made to inflate retention balloon 106 when catheter 100 is improperly inserted, etc.). Consequently, inflated retention balloon 106 will fill secondary balloon 116, causing secondary balloon 116 to inflate at the same time that retention balloon 106 deflates or remains deflated, depending on the circumstances.

In some embodiments, retention balloon 106 may be configured to inflate before secondary balloon 116, such as by having a modified wall than that of secondary balloon 116 in terms of thickness, durometer, or compliance. Thus, even if a portion of the injected fluid 206 is shunted to secondary balloon 116 (e.g., fluid 208), retention balloon 106 will inflate before secondary balloon 116 inflates. However, if external force is applied to retention balloon 106, this additional force onto the fluid in retention balloon 106 will create additional fluid pressure within secondary balloon 116, thereby inflating secondary balloon 116.

In other words, the fluid of retention balloon 106 and secondary balloon 116 may be in series with one another and interconnected by a third lumen/fluid channel. This allows retention balloon 106 to inflate, primarily, and independently of secondary balloon 116. If the pressure exerted on retention balloon 106 is greater than the resistance of the third lumen 204, plus the resistance of secondary balloon 116, retention balloon 106 may deflate by transferring fluid to secondary balloon 116, thereby mitigating tissue damage due to unintended traumatic catheter extraction with an inflated retention balloon 106.

In another embodiment, this functionality can be achieved by third lumen 204 being configured with a check valve that is activated only when the fluid pressure within retention balloon 106 exceeds a particular threshold (e.g., when retention balloon 106 is surrounded by tissue due to improper insertion of catheter 100, etc.).

Figure 3B:
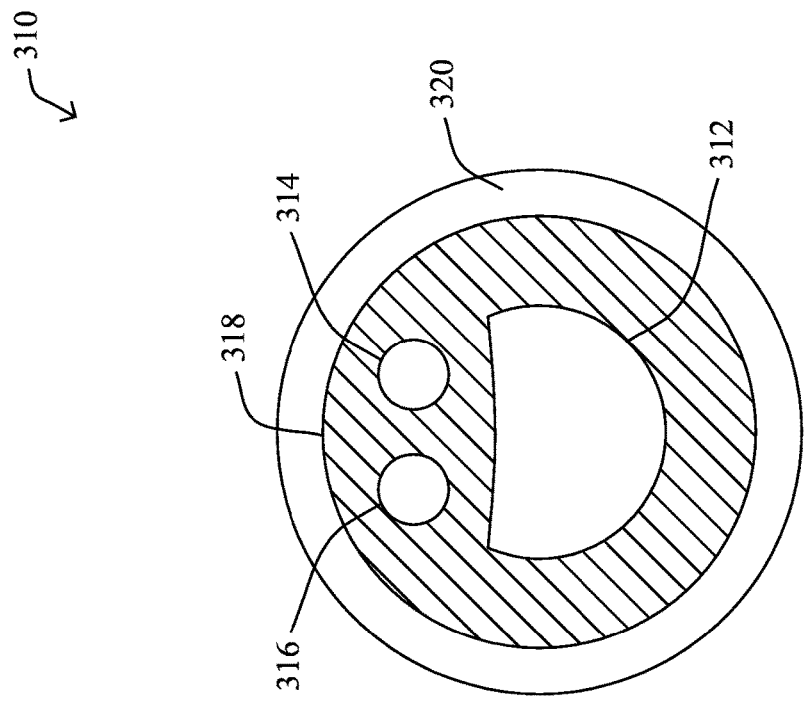
FIGS. 3A-3B illustrate cross-sectional views of a safety catheter, according to various embodiments.
Figure 3A:
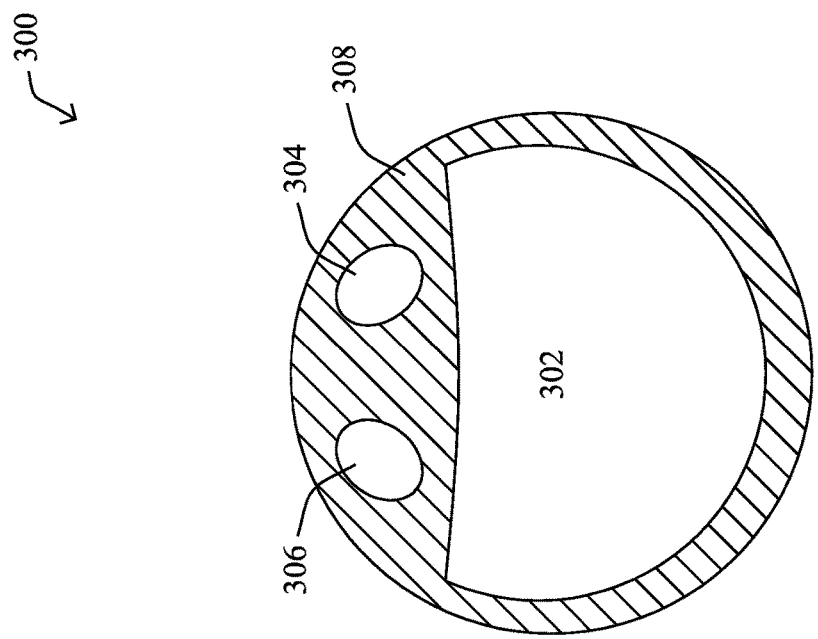

FIGS. 3A-3B illustrate cross-sectional views of a safety catheter, according to various embodiments. In particular, FIGS. 3A-3B illustrate alternative configurations for elongated member 104 described previously in FIGS. 1A-1C. As would be appreciated, the cross sections shown in FIGS. 3A-3B are illustrative only and other configurations can be used to implement the teachings herein.

In FIG. 3A, cross section 300 illustrates a possible configuration whereby the elongated member of the catheter is formed of a singular material 308 (e.g., latex, silicone, vinyl, plastic, etc.) such that three lumens are defined within the elongated member: a drainage lumen 302 that allows a fluid to drain from a subject (e.g., urine), a second lumen 304 that allows an injected fluid to be conveyed to a retention balloon of the catheter, and a third lumen 306 that shunts fluid from the retention balloon to a secondary balloon that remains ex vivo of the subject. Here, drainage lumen 302 may be of a substantially hemispherical shape and have a cross sectional area greater than that of either of lumens 304-306. Lumens 304-306 may themselves be of an ovular shape and formed within the catheter opposite that of drainage lumen 302.

In FIG. 3B, cross section 310 represents an alternative configuration for the elongated member of the catheter. In this configuration, an outer wall 320 may house a material 318 that defines three lumens: a drainage lumen 312, a second lumen 314 that connects the fluid inlet port of the catheter to its retention balloon, and a third lumen 316 that shunts fluid from the retention balloon to a second, ex vivo balloon of the catheter. In this configuration, lumens 314-316 are of substantially cylindrical shapes. Drainage lumen 312 retains a greater cross-sectional area than that of lumens 314-316, but less than that of cross section 300 in FIG. 3A. In addition, drainage lumen 312 may be of a more concave shape than that of drainage lumen 302.

As would be appreciated, cross section 300 and cross section 310 are exemplary in nature and other configurations for three lumens within a catheter are possible. For instance, while lumens 304-306 and 314-316 are located on the same side of their respective drainage lumens 302, 312, respectively, further embodiments provide for these lumens to be separated by the drainage lumen. In addition, while the three lumens are shown having the specific shapes, sizes, and relative sizes shown, these parameters can be varied, as desired.

Figure 4:
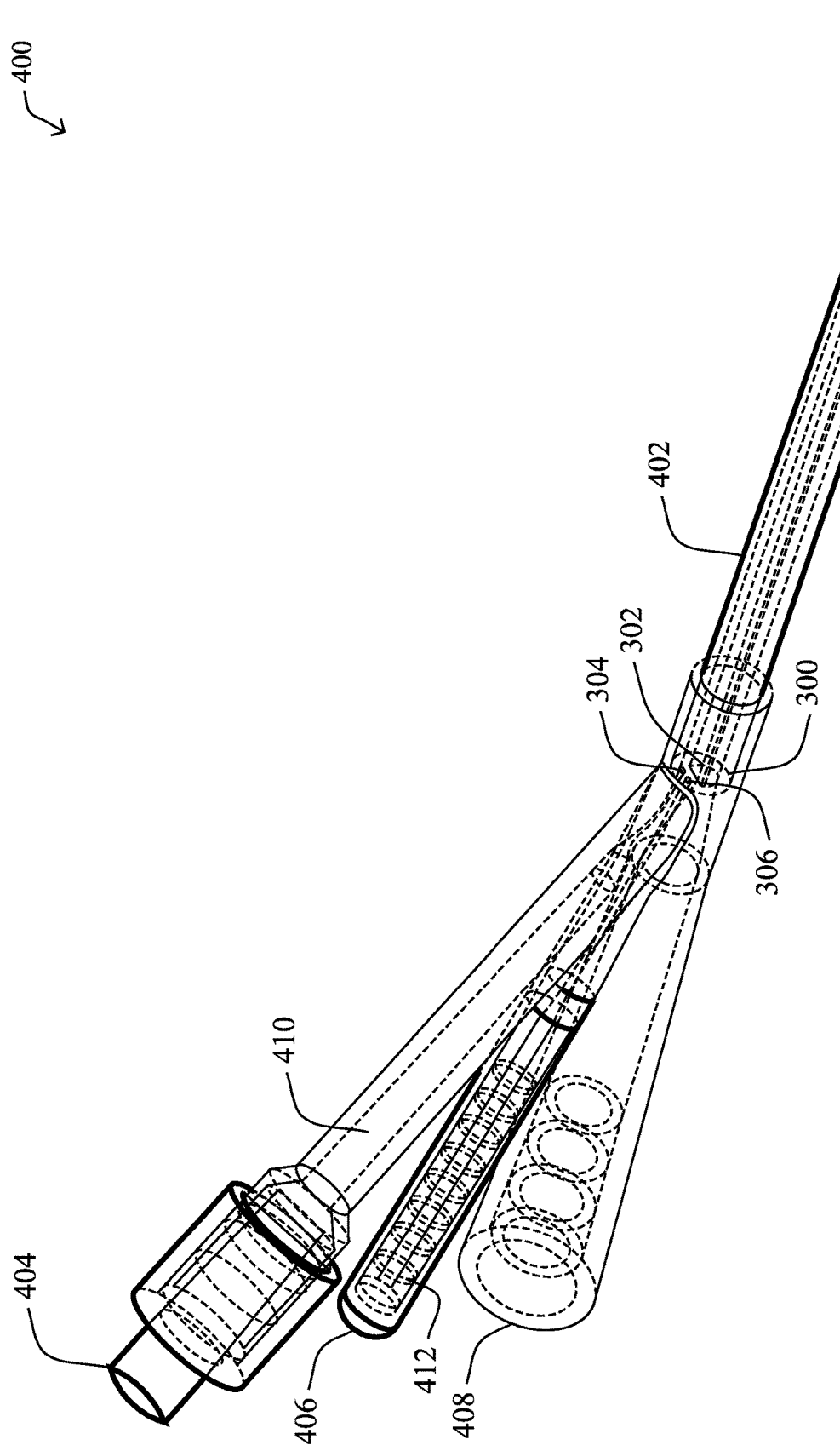
FIG. 4 illustrates a perspective view of a distal end of a safety catheter, according to various embodiments.

FIG. 4 illustrates a perspective view of a distal end of a safety catheter 400, according to various embodiments. In the embodiment shown, safety catheter 400 may operate in a similar manner to that of catheter 100 described previously with respect to FIGS. 1A-1C. More specifically, safety catheter 400 may comprise an elongated member 402 having a cross section 300, shown previously in FIG. 3 through which three lumens extend.

In contrast to the configuration of catheter 100 in which the protruding branches for its fluid inlet valve and second balloon are on opposing sides of its elongated member, the branches of safety catheter 400 are constructed to be substantially on the same side of elongated member 402. More specifically, for ease of manufacture, the drainage lumen 302 of elongated member 402 may terminate at drainage outlet 408. Protruding from elongated member 402 may also be branch 410 that connects fluid inlet valve 404 to second lumen 304 within elongated member 402, to convey injected fluid to the retention balloon of safety catheter 400 (not shown). Finally, safety catheter 400 may also include branch 406 that includes second balloon 412 that is connected to the retention balloon of safety catheter 400 via third lumen 306. In various embodiments, branches 406 and 410 may be substantially in line with one another, located on different sides of catheter 400, or using different relative locations, as desired.

In further embodiments, an elastomer/plastic sleeve may be placed over the secondary balloon during catheter placement into the subject. In another embodiment, the secondary balloon of the catheter disclosed herein may be pre-inflated, prior to packaging, to decrease the inflation pressure of the retention balloon, to ensure that the retention balloon inflates prior to the secondary during normal conditions. In yet another embodiment, the secondary balloon may be omitted in favor of a "pop-off" mechanism that allows fluid in the third lumen to be externalized from the catheter, should the pressure in the third lumen exceed a threshold associated with the mechanism.

Figure 5:
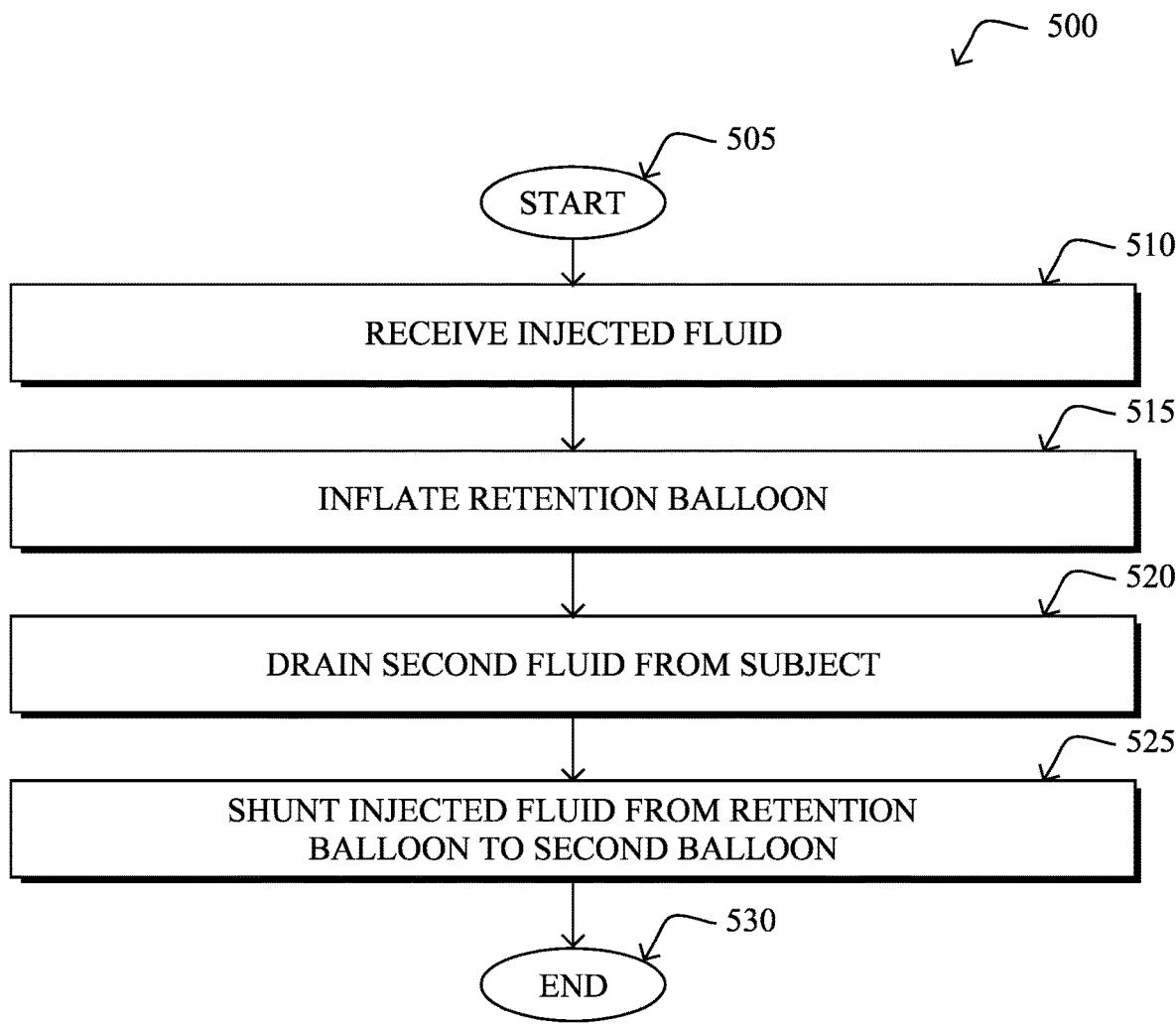
FIG. 5 illustrates an example procedure for operating a catheter, according to various embodiments.

FIG. 5 illustrates a simplified procedure 500 for operating a catheter, according to various embodiments. As shown, procedure 500 may start at step 505 and continue on to step 510 where, as described in greater detail above, the catheter may receive fluid via a fluid injection port located at its distal end. In general, the catheter may define a first lumen that connects a drainage inlet located at its proximal end to a drainage outlet at its distal end. For instance, a person administering the catheter to a subject may inject saline or another suitable fluid into the fluid inlet valve. As would be appreciated, in other embodiments, the catheter herein may be inflated with an alternate media, such as a gas, in other embodiments.

At step 515, as detailed above, the catheter may inflate a retention balloon of the catheter, in response to the received fluid injected in step 510. More specifically, the catheter may do so by conveying the injected fluid via a second lumen of the catheter into the retention balloon, thereby causing it to inflate. In general, the retention balloon may be located between the drainage inlet and the drainage outlet, allowing the proximal end of the catheter to be retained within the subject when the retention balloon is inflated.

At step 520, the catheter may drain a second fluid from the subject, as described in greater detail above. For instance, the catheter may receive urine or other bodily fluid via a drainage inlet located at its proximal end and convey it via its first, drainage lumen, to the drainage outlet of the catheter.

At step 525, as detailed above, the catheter may shunt, via a third lumen of the catheter and in response to an external force applied to the retention balloon, the first fluid from the retention balloon into a secondary balloon of the catheter. In various embodiments, this may be done in response to the retention balloon of the catheter experiencing an external force, such as due to an attempt to remove the catheter while the retention balloon is inflated, or the catheter is improperly inserted into the subject. By shunting the fluid to the second balloon, which may remain ex vivo, this allows the person administering the catheter to visually identify that a problem exists. In addition, by shunting fluid away from the retention balloon, this also helps to prevent traumatic injury to the subject. Procedure 500 then ends at step 530.

It should be noted that while certain steps within procedure 500 may be optional as described above, the steps shown in FIG. 5 are merely examples for illustration, and certain other steps may be included or excluded as desired. Further, while a particular order of the steps is shown, this ordering is merely illustrative, and any suitable arrangement of the steps may be utilized without departing from the scope of the embodiments herein.

As will be appreciated, the above examples are intended only for the understanding of certain aspects of the techniques herein and are not limiting in nature. While the techniques are described primarily with respect to a particular device or system, the disclosed processes may be executed by other devices according to further implementations. For example, while the techniques herein are described primarily with respect to employing a catheter to drain urine from a subject, the devices and techniques introduced herein are not limited as such and can be adapted for use during other forms of procedures, as well, without undue experimentation.

The foregoing description has been directed to specific embodiments. It will be apparent, however, that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A catheter comprising:
    an elongated member having a distal end and a proximal end, wherein:
        the proximal end defines a drainage inlet extending from an external wall of the elongated member into the elongated member; and
        the elongated member defines a first lumen that connects the drainage inlet with a drainage outlet defined by the distal end;
    an inflatable retention balloon defined by the external wall of the elongated member and located between the drainage inlet and the drainage outlet;
    a fluid inlet valve that protrudes from the elongated member and defines a second lumen that extends from the fluid inlet valve through the elongated member and to the inflatable retention balloon; and
    a secondary balloon that protrudes from and forms a closed end of the elongated member, the elongated member defining a third lumen that extends from the inflatable retention balloon to the secondary balloon.

2. The catheter as in claim 1, wherein the secondary balloon protrudes from the elongated member at the distal end of the elongated member.

3. The catheter as in claim 1, wherein the fluid inlet valve protrudes from the elongated member at the distal end of the elongated member.

4. The catheter as in claim 1, wherein the inflatable retention balloon is configured to inflate in response to fluid being injected into the fluid inlet valve.

5. The catheter as in claim 1, wherein fluid is shunted from the inflatable retention balloon towards the distal end of the elongated member and into the secondary balloon via the third lumen.

6. The catheter as in claim 5, wherein the fluid is shunted in response to an external force being applied to the inflatable retention balloon resulting from an attempt to remove the catheter from a subject while the inflatable retention balloon is inflated.

7. The catheter as in claim 5, wherein the fluid is shunted in response to an external force being applied to the inflatable retention balloon resulting from the catheter being inserted into a subject in a manner that generates more than a threshold amount of resistance to an inflation of the inflatable retention balloon.

8. The catheter as in claim 1, wherein the secondary balloon is configured to remain ex vivo to a subject while the inflatable retention balloon retains the drainage inlet of the elongated member in a hollow viscera of the subject.

9. The catheter as in claim 1, wherein the drainage outlet is configured to remain ex vivo to a subject while the inflatable retention balloon retains the drainage inlet of the elongated member in a urinary bladder of the subject, and wherein urine in the urinary bladder flows into the drainage inlet and out of the drainage outlet via the first lumen.

10. The catheter as in claim 1, wherein the drainage outlet has a diameter larger than that of the first lumen.

11. The catheter as in claim 1, wherein the first lumen has a larger diameter than that of the second lumen and of the third lumen.

12. A method comprising:
    receiving, via a fluid inlet valve of a catheter a first fluid injected into a second lumen defined by the catheter, the catheter also defining a first lumen that connects a drainage inlet at a proximal end of the catheter to a drainage outlet at a distal end of the catheter;
    inflating a retention balloon of the catheter by conveying the first fluid from the second lumen into the retention balloon, the retention balloon being located between the drainage inlet and the drainage outlet;
    draining a second fluid from a subject by conveying the second fluid from the drainage inlet to the drainage outlet via the first lumen; and
    shunting, via a third lumen of the catheter and in response to an external force applied to the retention balloon, the first fluid from the retention balloon into a secondary balloon of the catheter, wherein the secondary balloon forms a closed end of the third lumen.

13. The method as in claim 12, wherein the external force is caused by an attempt to remove the catheter from the subject while the retention balloon is inflated.

14. The method as in claim 12, wherein the external force is caused by the catheter being inserted into the subject in a manner that generates more than a threshold amount of resistance to an inflation of the inflatable retention balloon.

15. The method as in claim 12, further comprising:
    retaining, by the retention balloon, the drainage inlet within a urinary bladder of the subject, wherein the second fluid drained from the subject comprises urine.

16. The method as in claim 15, wherein the secondary balloon and the fluid inlet valve is configured to remain ex vivo to the subject while the retention balloon retains the drainage inlet within the urinary bladder of the subject.

17. The method as in claim 12, wherein the fluid inlet valve protrudes from the catheter at the distal end of the catheter.

18. The method as in claim 12, wherein the first lumen has a larger diameter than that of the second lumen and of the third lumen.

19. The method as in claim 12, wherein the secondary balloon protrudes from the catheter at the distal end of the catheter.

20. A catheter comprising:
- means for retaining the catheter in a hollow viscera of a subject;
- means for draining a first liquid from the hollow viscera of the subject;
- means for inflating, with an inflation means, the means for retaining the catheter in the hollow viscera of the subject; and
- means for shunting the fluid from the means for retaining the catheter in the hollow viscera of the subject to a balloon forming a closed end to the means for shunting.

\* \* \* \* \*